United States Patent [19]

Beilfuss et al.

[11] Patent Number: 5,516,510
[45] Date of Patent: May 14, 1996

[54] DEODORIZING ACTIVE INGREDIENTS

[75] Inventors: Wolfgang Beilfuss; Heinz Eggensperger, both of Hamburg; Karl-Heinz Diehl, Norderstedt; Peter Oltmanns, Hamburg, all of Germany

[73] Assignee: Reckitt & Colman Inc., Montvale, N.J.

[21] Appl. No.: 158,122

[22] Filed: Nov. 24, 1993

[30] Foreign Application Priority Data

Nov. 26, 1992 [DE] Germany .................. 42 40 674.9

[51] Int. Cl.$^6$ .................. A61K 7/32; A61K 31/045; A61K 31/07
[52] U.S. Cl. .................. 424/65; 514/724; 514/725
[58] Field of Search .................. 424/65; 514/724, 514/725

[56] References Cited

U.S. PATENT DOCUMENTS

| | | | |
|---|---|---|---|
| 2,467,884 | 4/1949 | Elias | 514/724 |
| 3,652,764 | 3/1972 | Lamberti et al. | 424/235 |
| 5,171,577 | 12/1992 | Griat et al. | 514/945 |

FOREIGN PATENT DOCUMENTS

| | | | |
|---|---|---|---|
| 0216303 | 4/1987 | European Pat. Off. | A61K 47/00 |
| 0297310 | 1/1989 | European Pat. Off. | A61K 7/32 |
| 4026756 | 2/1992 | Germany | A01N 47/44 |
| 4124664 | 1/1993 | Germany | A01N 31/04 |

OTHER PUBLICATIONS

Nakamura et al, Chem Abs, 108:118746, Abstract of Europat 245756, Nov. 19, 1987.
Griat et al, Chem. Abs., 114:171043, Abs. of Eur. Pat. Appln. 382,618, Aug. 16, 1990 (equivalent to U.S. Pat. 5,171,577).
Chem. Abs., vol. 108:118746, Abstract of Europat 87–106509 (May 5, 1987) (Nakamura et al).
Chem. Abs., vol. 114:171043, Abstract of Europat 382619 (Aug. 16, 1990) (Griat et al).
Wedderburn, D. L., "Personal Deodorants", in Handbook of Cosmetic Science, pp. 454–457 (1963).
deNavarre, M. G., "The Chemistry and Manufacture of Cosmetics", pp. 215–216 (2d ed. 1975).

*Primary Examiner*—Shelley A. Dodson
*Attorney, Agent, or Firm*—Frederick H. Rabin; J. Jeffrey Hawley

[57] ABSTRACT

Deodorant compositions comprise glycerin monoalkyl ethers of the formula

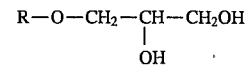

in which R is a branched or unbranched $C_6$–$C_{18}$ alkyl in combination with other deodorant ingredients. Preferably R is $C_8$ to $C_{12}$ alkyl; more particularly, $C_8$ alkyl; and most preferably, 2-ethylhexyl.

6 Claims, No Drawings

DEODORIZING ACTIVE INGREDIENTS

The invention relates to compounds with deodorizing action and in particular to their use for banishing unpleasant odors caused by microorganisms.

Body odor arises when sweat, odorless in itself, is decomposed by microorganisms. Above all gram-positive germs found on the skin are able to form from the sweat contents, the sebum and remains of cell skin substances, which have an unpleasant odor. These microbially-produced substances not only propagate bad odor but can also cause skin irritation.

To avoid unpleasant body odor the following possibilities (active principles) are, for example, known:

a) The secretion of sweat can be reduced or banished by astringents, in particular predominantly aluminum salts such as aluminum hydroxychloride. Astringents denaturize the skin proteins and dramatically influence the heat balance of the axilla region.

b) The bacterial flora on the skin can be reduced by antimicrobial substances. In the ideal case, only those microorganisms causing the odor should be destroyed here. In most cases, however, the entire micro-flora of the skin is damaged. Sometimes the microbes which cause no odor are even more severely damaged.

c) Body odor can be concealed by fragrances. At times, however, the mixture of body odor and perfume can also smell unpleasant rather than not.

To reduce the formation of unpleasant odor caused by microorganisms by means of antimicrobial substances the use of, for example, 5-chloro-2-(2,4-dichlorophenoxy)phenol (Irgasane DP 300) and/or farnesol combined with phenoxyethanol or optionally in the presence of glycerin monolaurate as a deo-active ingredient is known. The use of this known active ingredient combination does, however, have disadvantages. Irgasane DP 300 is, admittedly, very effective, but does contain organically bound halogen and is therefore not very environmentally compatible, since the formation of highly toxic dioxins during production or thermal decomposition cannot be ruled out. Farnesol combined with phenoxyethanol and/or glycerin monolaurate is not sufficiently effective against the odor-causing microorganisms in all cases. In addition, this active ingredient combination has a rather non-specific effect against gram-positive and gram-negative bacteria.

The object underlying the invention is to avoid these disadvantages and make available new deodorizing active ingredients (deo-active ingredients) or active ingredient combinations which show a good effect in particular against the gram-positive bacteria which are particularly relevant from the point of view of causing odor, act selectively against odor causing microorganisms whilst largely sparing the natural flora of the skin, adhere well to the skin and display an excellent stability and, moreover, are low in, or neutral in terms of odor.

To achieve the object according to the invention, it is proposed to use glycerin monoalkylethers of the general formula

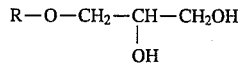

in which R is a branched or unbranched $C_6$–$C_{18}$ alkyl group, whereby the alkyl group can be substituted by one or more hydroxy and/or $C_1$–$C_4$ alkoxy group(s), and/or the alkyl chain can be interrupted by up to four oxygen atoms, i.e. can contain alkylenoxy groups such as ethylenoxy- and propylenoxy groups, individually or in the form of a mixture of two or more of the same, as deo-active ingredient to banish unpleasant odors.

Preferred versions are the subject of the dependent claims.

It was surprisingly found that 3-(alkyloxy)propane 1,2-diols (glycerin monoalkylethers) of the formula

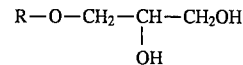

have a good deodorizing effect.

The radical R is preferably a $C_8$–$C_{12}$ alkyl group and, in particular, a 2-ethyl hexyl group or dodecyl group, of which 2-ethyl hexyl is the most preferred. 2-ethyl hexyl glycerin ether of a specifically low-odor peroxide-free grade is particularly preferred.

Further, it was found that a mixture of two or more of these glycerin monoalkyl ethers can be used advantageously, mixtures of 2-ethyl hexyl glycerin ether and dodecyl glycerin ether being preferred.

It is assumed that the surprising deodorizing effect of the glycerin monoalkyl ethers according to the invention can be based on several different effect mechanisms.

1) The glycerin ethers have an antimicrobial effect, a good effect being achieved in particular with gram-positive, odor-causing bacteria.

2) The glycerin ethers inhibit enzymes or catalysts which are responsible for the odor formation from the primarily odorless sweat.

3) The glycerin ethers have an effect on the sweat-gland secretion, whereby sweat secretion is reduced.

4) The glycerin ethers cover up or absorb the odor-intensive sweat components or interact with them, e.g. through bonding via hydrogen bridges, formation of complexes or inclusions.

5) The glycerin ethers operate through other still unknown mechanisms which finally contribute to a clearly surprising deodorizing effect.

It is particularly surprising that, for example, 2-ethyl hexyl glycerin ether displays such a good deodorizing effect despite its water solubility of ca. 0.2 wt. % which is still good compared with known deo-active ingredients. As well as the anti-microbial effectiveness and the other possible action mechanisms mentioned above, the good spreading capacity, good penetration capacity into the skin and/or the ability to penetrate deeper into the upper layers of the epidermis may also possibly be decisive.

The glycerin monoalkyl ethers according to the invention display in particular the advantageous properties listed below:

good to very good action, particularly against the gram-positive bacteria which are particularly relevant from the point of view of causing odor selective action against odor-causing microorganisms whilst largely sparing the natural skin flora good adhesion to the skin limited to little water solubility (sufficiently water-resistant)

excellent stability (hydrolysis stability, thermal stability, pH stability)

practically non-volatile colorless, neutral pH, inert low in odor or specifically neutral in terms of odor if a selected grade is used partly liquid and therefore easily processable, no crystallization in the preparation and on the skin compatible with other active ingredients and auxiliaries support for the dispersing and co-emulsifying action in cosmetic preparations the glycerin monoalkylether structure is found in numerous naturally occurring compounds because of the broad additional benefit provided by glycerin monoalkyl ethers in cosmetic preparations, other cosmetic additives can be partially dispensed with or their quantities reduced.

Since the glycerin monoalkyl ethers according to the invention are mild and skin-compatible, have a good spreading capacity and confer a pleasant skin feeling, they are particularly suitable for deo-compositions.

The glycerin monoalkyl ethers according to the invention can be used individually, in the form of a mixture of two or more of same and, moreover, combined with one or more other deodorizing substances. These are preferably antiperspirants (astringents), substances with an anti-microbial action and/or fragrances. Preferred are skin-compatible (substantive) active ingredients, insoluble in water or soluble in water to a limited extent, with specific action against odor-causing microorganisms and/or naturally occurring deodorizing active ingredients. Particularly suitable as co-active ingredients are naturally occurring substances having a deodorizing action such as farnesol, phenoxy ethanol, glycerin monolaurate, alkalirhodanides, linalool, citronellol, geraniol and phenethyl alcohol, the low-odor substances being preferred. Further, examples of active ingredients with odor-reducing action are aluminum oxychloride, dibromodicyanobutane, 5-chloro-2-(2,4-dichlorophenoxy) phenol (Irgasans DP 300), 2-bromo 2 nitropropane diol-1,3 (Bronopole), chlorohexidine salts, octenidine salts, alexidine salts as well as salts of other cation-active compounds with deodorizing action, the rhodanide salts being preferred. Particularly preferred are farnesol and phenoxy ethanol.

If a combination of the glycerin monoalkyl ethers with such other deo-active ingredients/antiperspirants is used, synergistic increases in effect are also observed in some cases.

The glycerin monoalkyl ethers according to the invention are used in a concentration in the range 0.01 to 20 wt. % relative to the ready-to-use deo-composition. The concentration is preferably in the range 0.1 to 15 wt. % and in particular in the range 0.5 to 10 wt. %.

The ratio of glycerin monoalkyl ether to the other composition component(s) having a deodorizing action is in the range 50:1 to 1:50, preferably 10:1 to 1:10 and particularly preferably in the range 5:1 to 1:1.

In the finished working solution the deo-active ingredients according to the invention are present in an aqueous and/or alcoholic medium. The alcohols suitable for forming the alcoholic medium or the alcoholic components of the medium include $C_2$–$C_3$ alkanols, glycols and polyglycols. In particular, the $C_2$–$C_3$ alkanols comprise ethanol, propanol, isopropanol and/or mixtures of them, and the polyglycols comprise polyethylene glycol, polypropylene glycol and/or mixtures of them. Mixtures of glycerin monoalkylethers and lower alcohols such as, for example, ethanol have a distinct synergistic anti-microbial effectiveness which could be additionally exploited, since ethanol is frequently used as a constituent of deo-formulations. In addition, the alcohols can serve as solubilizers. In comparison, glycols and polyglycols display no antimicrobial properties exploitable according to the invention.

The invention relates not only to the use of the glycerin monoglycol ethers according to the invention, alone or combined with other substances having a deodorizing action, but furthermore to the corresponding compositions of glycerin monoalkyl ether and one or more other substances with a deodorizing action selected from astringents, skin-compatible (substantive) active ingredients, insoluble in water or soluble in water to a limited extent, with specific action against odor causing microorganisms and/or naturally occurring deodorizing active ingredients. Particularly preferred here are compositions which contain, as well as glycerin monoalkyl ether, farnesol, phenoxyethanol or glycerin monolaurate.

These compositions are produced by mixing the individual components together, optionally with warming.

The invention is described in more detail below with reference to embodiments.

The formulations given in the following table were tested in the agar hole test for effectiveness against deo-germs, the microbiological effectiveness being given as the diameter of the corresponding zone of inhibition in mm.

TABLE

| Formulation | POE | GE | Farnesol | PLG |
|---|---|---|---|---|
| Example 1 | | | | |
| (a) | | 0.4 | 0.1 | 6.5 |
| (b) | | 0.2 | 0.05 | 6.75 |
| (c) | | 0.1 | 0.025 | 6.875 |
| (d) | | 0.05 | 0.0125 | 6.9375 |
| Example 2 | | | | |
| (a) | 0.4 | | | 6.6 |
| (b) | 0.2 | | | 6.8 |
| (c) | 0.1 | | | 6.9 |
| (d) | 0.05 | | | 6.95 |
| Example 3 | | | | |
| (a) | 0.4 | | 0.1 | 6.5 |
| (b) | 0.2 | | 0.05 | 6.75 |
| (c) | 0.1 | | 0.025 | 6.875 |
| (d) | 0.05 | | 0.0125 | 6.9375 |
| Example 4 | | | | |
| (a) | | 0.4 | | 6.6 |
| (b) | | 0.2 | | 6.8 |
| (c) | | 0.1 | | 6.9 |
| (d) | | 0.05 | | 6.95 |
| Example 5 | | | | |
| (a) | | | 0.1 | 6.9 |
| (b) | | | 0.05 | 6.95 |
| (c) | | | 0.025 | 6.975 |
| (d) | | | 0.0125 | 6.9875 |
| Example 6 | | | | 7.0 |

Microbiological effectiveness, data in mm inhibition zone diameter:

| Formulation | SA gram + | SE gram + | ML gram + | PM gram − | KP gram − | EG gram − |
|---|---|---|---|---|---|---|
| Example 1 | | | | | | |
| (a) | 18 | 18 | 23 | 12 | 25 | 20 |
| (b) | 18 | 18 | 23 | 12 | 25 | 18 |
| (c) | 18 | 18 | 23 | 12 | 25 | 17 |
| (d) | 18 | 18 | 23 | 12 | 20 | 15 |
| Example 2 | | | | | | |
| (a) | 13 | 14 | 14 | 19 | 20 | 20 |
| (b) | 0 | 0 | 11 | 14 | 15 | 18 |
| (c) | 0 | 0 | 0 | 11 | 11 | 12 |
| (d) | 0 | 0 | 0 | 11 | 0 | 11 |
| Example 3 | | | | | | |
| (a) | 18 | 16 | 24 | 17 | 21 | 20 |
| (b) | 17 | 15 | 18 | 14 | 16 | 11 |
| (c) | 15 | 15 | 18 | 0 | 14 | 0 |
| (d) | 15 | 13 | 17 | 0 | 14 | 0 |
| Example 4 | | | | | | |
| (a) | 19 | 18 | 24 | 12 | 23 | 23 |
| (b) | 18 | 18 | 24 | 12 | 23 | 23 |
| (c) | 18 | 18 | 24 | 12 | 23 | 20 |
| (d) | 16 | 18 | 22 | 11 | 21 | 16 |
| Example 5 | | | | | | |
| (a) | 14 | 13 | 18 | 0 | 12 | 0 |
| (b) | 14 | 13 | 17 | 0 | 12 | 0 |
| (c) | 14 | 13 | 16 | 0 | 12 | 0 |
| (d) | 14 | 13 | 15 | 0 | 12 | 0 |
| Example 6 | 0 | 0 | 0 | 0 | 1 | 0 |

Key:
Microorganisms
SA *Staphylococcus aureus*
SE *Staphylococcus epidermis*
ML *Micrococcus luteus*
PM *Proetus mirabilis*
KP *Klebsiella pneumonias*
FG *Enterobacter gergoviae*
Raw products
POE 2-phenoxy ethanol
GE 2-ethylhexyl glycerin ether
PLG 1,2-propylene glycol Plate diffusion test
1. Agar hole test
   Bacteria: 18–24 hour bouillon cultures are diluted 1:4 (1 ml bacteria suspension+3 ml CSL). Yeast: a 4-day-old *Candida albicans* culture (CSA+ grape sugar) is flooded with 5 ml physiological cooking salt solution and set according to a barium sulfate standard.
   0.2 ml of the bacteria suspension are spread on CSA.
   0.1 ml of the *Candida albicans* suspension are spread on CSA.
   A hole with a diameter of 8 mm is punched in the center of the agar plates using a scorched cork borer.
   This hole is filled to the rim with the preparation to be tested.
   The plates are left to stand for two hours at room temperature to prediffuse.
   Bacteria and yeast are incubated at 370° C. for 24–48 hours.
   Evaluation: zone of inhibition in mm starting from the rim of the hole.
CSA=Casein peptone-soya flour peptone agar
CSL=Casein peptone-soya flour peptone solution
The following information regarding the deo-effectiveness of the preparations can be deduced from the results of the agar hole zone of inhibition test: definitely better than deodorants customary in the trade. With a single application in the morning, a protection against odor development was observed over the whole day and even longer.

The suitability of the glycerin ethers according to the invention as a deo-active ingredient in combination with other deo-active ingredients has also been investigated using the so called sniffing test. Active ingredient formulations were investigated which contain 2-ethyl glycerin ether in combination with other deo-active ingredients or only other deo-active ingredients. Testing was by means of pair comparison. The test method is described in "dragoco report" 6/76.

1. 20 healthy male and female adults who are known have a problem with sweat odor are included in the test. The subjects are instructed to use an unperfumed soap without anti-bacterial active ingredients under their arm-pits for 10 days before the start of the test. No cosmetics are used in this region of the body for the whole of the test period. Only the unperfumed soap is used once a day.

2. On the 11th day, 5 hours after the last wash, the arm pits of 3 candidates are smelled (sniffed) for odor and judged according to grades 0 to 5:
   0=no sweat odor
   1=very slight sweat odor
   2=slight sweat odor
   3=moderate sweat odor 4=strong sweat odor 5=very strong sweat odor The pair comparison (left against right arm pit) for each subject is decisive for the verdict. Noticeable pairwise differences are judged with at least one grade difference. The starting values must not be less than grade 3.

3. The deo-formulations are then issued to the candidates with the instruction that the products are used in the standard way for a period of 5 days. 10 subjects apply DEO-A under the right arm pit and Deo-B, C or D under the left arm-pit, 10 subjects apply the products in exactly the reverse manner.

4. On the 5th product-use day, 5 hours after the last application, sniffing and grading is carried out once again.

5. In order to obtain results reflecting conditions encountered in practice, no standardization of clothing is undertaken.

Evaluation

The individual grades were averaged and the standard deviation calculated. In order to test whether a difference exists between the pair-tested deo-formulations or whether a difference is detectable between the starting value and the end value of each formulation, the pairwise t-test (Lothar Sachs, Angewandte Statistik, Springer Verlag, 6th edition, 1984, pages 242–244) was carried out and checked with the Dixon and Mood sign test (Lothar Sachs, Angewandte Statistik, Springer Verlag, 6th. edition, 1984, pages 247–250). To compare the pairwise-tested products, the paired individual value differences were used.

| Deo-formulations for the sniff test | | | | |
|---|---|---|---|---|
| | A | B | C | D |
| Irgasan ® DP 300 | 0.1 | | | |
| Dibromodicyanobutane | | 0.015 | | |
| Quartamine active ingredient | | | 0.2 | |
| Sodium thiocyanate | | | 0.038 | |
| Octenidine dihydrochloride | | | | 0.1 |
| Phenoxyethanol | | 0.15 | 1.762 | |
| 2-ethylhexyl glycerin ether | | 0.135 | | 0.9 |
| 1,2-propylene glycol | 1.0 | 1.0 | 1.0 | 1.0 |
| Ethanol, DEP denatured | 40.0 | 40.0 | 40.0 | 40.0 |
| Demineralized water | 58.9 | 58.7 | 57.0 | 58.0 |

*N-benzyl-N-(2-hydroxyethyl)-N-(lauroyloxyethyl)-N-methyl ammonium chloride

Results:

| Product comparison | average starting values A B, C & D | average final values A B, C & D | noticeable difference |
|---|---|---|---|
| Deo-A/Deo-B | 4.03 4.08 | 3.28 3.00 | yes |
| Deo-A/Deo-C | 3.98 3.90 | 2.90 2.93 | no |
| Deo-A/Deo-D | 3.76 3.92 | 2.89 2.63 | yes |

All products in the test, even Deo-A, effect a reduction of the sweat odor in the axilla region after 5 days' use and 5 hours' break in application. There are clear signs that Deo-B and Deo-D show a better deo-effect than Deo-A. There are no significant differences between Deo-A and Deo-C as regards the deo-effect.

We claim:

1. An aqueous or alcoholic deodorizing composition for human body odor comprising
   (a) from 0.01 to 20 wt % of a deodorizing glycerin monoalkyl ether of the general formula

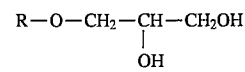

in which R is a branched or unbranched $C_8$–$C_{12}$ group, and
   (b) an effective amount of one or more substances selected from the group consisting of
      (i) astringent and other skin-compatible active ingredients with specific action against odor-causing bacteria, said ingredients selected from the group consisting of aluminum oxychloride, dibromodicyanobutane, 5-chloro-2-(2,4-dichlorophenoxy)-phenol, 2-bromo-2-nitropropane-diol-1, 3, octenidine salts and alexidine salts, and
      (ii) naturally occurring deodorizing active ingredients selected from the group consisting of farnesol, phenoxyethanol, glycerin monolaurate, alkali rhodanides, linalool, citronellol, geraniol and phenethyl alcohol.

2. The composition of claim 1 in which R is a $C_8$ group.

3. The composition of claim 2 in which R is 2-ethylhexyl.

4. The composition of claims 1, 2 or 3 in which the glycerin monoalkyl ether is present in a concentration in the range of from 0.1 to 15 wt %.

5. The composition of claim 4 in which the glycerin monoalkyl ether is present in a concentration in the range of from 0.5 to 10 wt %.

6. A method of deodorizing human body odors comprising the step of applying a composition according to claim 1 to the body part bearing the odor.

* * * * *